United States Patent [19]

Bowers et al.

[11] Patent Number: 5,599,587
[45] Date of Patent: Feb. 4, 1997

[54] PHOSPHORIC ACID ESTERS AND THEIR USE IN THE PREPARATION OF BIOCOMPATIBLE SURFACES

[75] Inventors: Roderick W. J. Bowers; Peter W. Stratford; Stephen A. Jones; Jeremy C. Russell; Michael J. Driver, all of Uxbridge, United Kingdom

[73] Assignee: Biocompatibles Limited, Middlesex, United Kingdom

[21] Appl. No.: 50,167

[22] PCT Filed: Nov. 5, 1991

[86] PCT No.: PCT/GB91/01934

§ 371 Date: Apr. 30, 1993

§ 102(e) Date: Apr. 30, 1993

[87] PCT Pub. No.: WO92/07858

PCT Pub. Date: May 14, 1992

[30] Foreign Application Priority Data

Nov. 5, 1990 [GB] United Kingdom ............... 9024011
Nov. 5, 1990 [GB] United Kingdom ............... 9024012

[51] Int. Cl.$^6$ ........................................ C07F 9/09
[52] U.S. Cl. .................... 427/322; 427/301; 568/14; 564/496; 564/503
[58] Field of Search ............... 427/2, 301, 322; 564/496, 503, 511; 568/14

[56] References Cited

FOREIGN PATENT DOCUMENTS

| 157469 | 10/1985 | European Pat. Off. . |
|---|---|---|
| 0332129 | 9/1989 | European Pat. Off. . |
| 0332129 | 9/1989 | European Pat. Off. . |
| 58-154591 | 9/1983 | Japan . |
| 60-184093 | 9/1985 | Japan . |
| 60-204791 | 10/1985 | Japan . |
| 60-204711 | 10/1985 | Japan . |
| 61-207395 | 9/1986 | Japan . |
| 2041377 | 9/1980 | United Kingdom . |
| WO91/13639 | 9/1991 | WIPO . |

OTHER PUBLICATIONS

Biomaterials, Hayward et al Biomembranes as models for polymer surfaces 1986, vol. 7, Jul. pp. 252–258.

Umeda et al Makromol Chem, Rapid Commun Jul. 1982 vol. 3 pp. 457–459 Polymeric Phospholipid Analogues.

Kurioka J. Biochemistry, 1968, vol. 63, No. 5, pp. 678–679 Synthesis of p–Nitrophenyl phosphorylcholine etc.

Chesebro et al Biochemistry, vol. 11, No. 5, 1972, pp. 766–771 Affinity Labeling of a Phosphorylcholine.

Volanakis et al J. Immunological Methods, 23, (1978) 285–295 C–Reactive Protein: Purification by Affinity etc.

Oliveira et al J. of Immunology vol. 124, No. 3, Mar. 1980 1396–1402 Comparative Studies on the Binding Properties of Human and Rabbitt etc.

J. Biological Chemistry vol. 256, No. 2, Jan. 25, 969–975, 1981 Robey et al "Limulin: A C–reactive Protein from Limulus polyphemus".

FEBS Letters vol. 88 No. 2, Apr. 1978 pp. 172–175 Pontet et al One Step Preparation of Both Human C–Reactive Protein etc.

Immunobiol. vol. 163, pp. 36–47 (1982) Uhlenbruck et al Two Different Anti–Galactan Lectins in Eel Serum Biochimie, 1979, 61, 1293–1299 Pontet et al Preparation et forme serique de la proteine etc.

Proc. Natl. Acad. Sci vol. 75 No. 9, pp. 4074–4077 Sep. 1978 Eibl Phospholipid synthesis: Oxazaphospholanes etc.

Pierce Immunotechnology Catalogue 1990, p. 35—Affinity Chromatography and Gel Permeation.

*Primary Examiner*—Glenn A. Caldarola
*Attorney, Agent, or Firm*—Sughrue, Mion, Zinn, Macpeak & Seas

[57] ABSTRACT

A process for the preparation of compounds of formula (I) in which Z is hydrogen or —NHZ is an activated amine group capable of reacting with a surface, the groups R are the same or different and each is a straight or branched $C_1$–$C_4$ alkyl group, preferably methyl, n is from 2 to 6, and X is a straight or branched $C_{1-20}$ alkylene group, or X is a group of formula —$(CH_2CH_2O)_b$—, or —$(CH_2)_c$—Ar—$(CH_2)_d$— where b is from 1 to 20, c and d are the same or different and each is from 0 to 5, and Ar is a para- or meta-disubstituted phenyl group (preferably a para-disubstituted phenyl group) which is optionally further substituted by one or more $C_1$–$C_4$ alkyl groups, or an acid addition salt thereof or a hydrate thereof, new compounds of formula (I) and salts and hydrates thereof and the use of compounds of formula (I) and salts and hydrates thereof in treating surfaces to render them more biocompatible.

39 Claims, No Drawings

PHOSPHORIC ACID ESTERS AND THEIR USE IN THE PREPARATION OF BIOCOMPATIBLE SURFACES

This invention relates to a new process for the preparation of compounds useful in the production of biocompatible surfaces, certain new compounds produced by the process, and a process for treating a surface with such compounds.

The clinical use of blood contacting devices and prostheses is of major importance today in cardiovascular surgery and other fields of medicine. Heart valves and blood vessel prostheses, balloon pumps and catheters are being implanted in daily surgical practice in restoration and diagnosis of cardiovascular function. Artificial organs are routinely employed in blood detoxification by absorptive haemoperfusion and in oxygenation (membrane oxygenators and heart-lung devices). Considerable effort and capital is invested in Europe and the U.S.A. in the development and experimental evolution of an implantable artificial heart system.

The devices are generally constructed from polymeric materials and, when in use, blood-polymer contact occurs. This contact will cause a reaction in the recirculating blood, which, depending on the choice of material, the design parameters, the flow or the addition of the anticoagulants, may lead to protein deposition, adhesion and destruction of red blood cells (haemolysis), platelet (thrombocyte) adhesion and aggregation and blood coagulation leading to formation of a haemostatic plug (thrombus). The occurrence of thromboembolism in cardiovascular surgery continues to be a problem, notwithstanding routine treatment with anticoagulants. For these reasons the search for biocompatible non-thrombogenic materials has been an important research objective over the last two decades.

Synthetic polymers are also widely employed in sight correction devices, such as soft, rigid, gas permeable and hard contact lenses and intra-ocular lenses. However, it is now well recognised that the performance of commonly employed polymer compositions can be hindered by the adsorption of tear proteins (such as lysozyme) at polymer interfaces. A variety of problems can then result such as reduction in gas permeability of the lens, discomfort to the patient and loss of visual acuity. Complete rejection of the lens is not uncommon.

Protein absorption can also cause serious problems in separation apparatus and other devices which come into contact extra-corporeally or intra-corporeally with protein solutions including body fluids. For example, polymeric particles and separation membranes can become fouled or blocked by such adsorption despite selection of the materials and careful design of the apparatus.

Biocompatible materials are also therefore of particular use in the treatment of polymeric materials for use as contact lenses. Such treatments help to improve the comfort of the wearer and in particular help to prevent the build up of protein deposits.

Our earlier patent application, EP-A-157,469 discloses compounds which aim to mimic the interfacial characteristics of the outer cell surface of red blood cells and platelets, and in particular the lipid component of the biological membrane which is the simplest common factor of all these surfaces. That application discloses compounds which are derivatives or analogues of phosphatidylcholine or phosphatidyl ethanolamine that can be covalently linked to the surface which is to be rendered biocompatible so as to deposit a phosphatidylcholine or phosphatidyl ethanolamine type of residue on a surface. Such residues are commonly found in lipid membranes.

We have now devised a new and more convenient process, which may be used to obtain some of the compounds of EP-A-157,469 in surprisingly pure form. These compounds moreover, show surprisingly increased biocompatibility over that disclosed in EP-A-157,469. Moreover the process also allows the preparation of new compounds.

Accordingly the present invention provides a process for the preparation of a compound of formula (I)

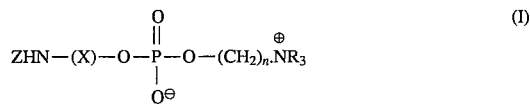

in which Z is hydrogen or —NHZ is an activated amine group capable of reacting with a surface, the groups R are the same or different and each is a straight or branched $C_1$–$C_4$ alkyl group, preferably methyl, n is from 2 to 6, preferably 2 to 4, more preferably 2, and X is a straight or branched $C_{1-20}$ alkylene group, preferably a group of formula —$(CH_2)_a$—, or X is a group of formula —$(CH_2CH_2O)_b$—, or —$(CH_2)_c$—Ar—$(CH_2)_d$— where a is from 1 to 20, b is from 1 to 20, c and d are the same or different and each is from 0 to 5, and Ar is a para- or meta-disubstituted phenyl group (preferably a para-disubstituted phenyl group) which is optionally further substituted by one or more $C_1$–$C_4$ alkyl groups, or an acid addition salt thereof or a hydrate thereof, which process comprises:

(a) reacting a protected compound of formula (II)

in which R' is a protecting group and R" is a protecting group or hydrogen, or R' and R" together form a protecting group, or NR'R" is $NH_3^{\oplus}A^{\ominus}$ in which $A^{\ominus}$ is a counterion, with a compound of formula (III)

in which n is from 2 to 4 and Hal is halogen, preferably chlorine, to provide a compound of formula (IV)

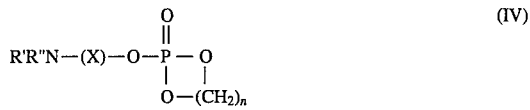

in which R',R" and X are as hereinbefore defined and n is from 2 to 4, reacting the compound of formula (IV) with $NR_3$, where R is as hereinbefore defined and where necessary or desirable, removing all protecting groups to provide a compound of formula (I) in which Z is hydrogen; or (b) reacting a compound of formula (V):

in which X is as hereinbefore defined, or a phosphate salt thereof, with a compound of formula (VI):

in which R is as hereinbefore defined, n is from 2 to 6 and each Hal is the same or different and is halogen, preferably bromine; to provide a compound of formula (I) in which Z is and hydrogen and if desired, converting the product thus obtained to a compound in which —NHZ is an activated amine group capable of reacting with a surface, and/or, if desired converting the product thus obtained to an acid addition salt or a hydrate.

As a further aspect the invention provides new compounds of formula (I) in which X is a group of formula $-(CH_2)_a-$, where a is from 11 to 20, or is a group of formula $-(CH_2CH_2O)_b-$ or $-(CH_2)_c-Ar-(CH_2)_d-$ as hereinbefore defined, or in which —NHZ is an activated amine group capable of reacting with a surface.

The invention also provides a process for treating a surface, for instance a polymeric surface, which comprises contacting the surface with a compound of formula (I) or salt or hydrate thereof.

According to a particular embodiment of this process, the compound of formula (I) is one in which Z is hydrogen.

In one specific embodiment the invention provides a process for the preparation of a compound of formula (Ia)

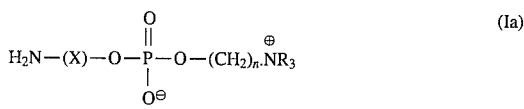

in which the groups R are the same or different and each is a straight or branched $C_1$–$C_4$ alkyl group, preferably methyl, n is from 2 to 4, preferably 2, and X is a straight or branched $C_{1-20}$ alkylene group, preferably a group of formula $-(CH_2)_a-$, or X is a group of formula $-(CH_2CH_2O)_b-$, or $-(CH_2)_c-Ar-(CH_2)_d-$ where a is from 1 to 20, b is from 1 to 20, c and d are the same or different and each is from 0 to 5, and Ar is a para- or meta- disubstituted phenyl group (preferably a para-disubstituted phenyl group) which is optionally further substituted by one or more $C_1$–$C_4$ alkyl groups, or an acid addition salt thereof or a hydrate thereof, which process comprises reacting a protected compound of formula (II)

R'R"N—(X)—OH    (II)

in which R' is a protecting group and R" is a protecting group or hydrogen, or R' and R" together form a protecting group, or NR'R" is $NH_3^{\oplus}A^{\ominus}$ in which $A^{\ominus}$ is a counterion, with a compound of formula (III)

in which n is as hereinbefore defined and Hal is a halogen, preferably chlorine, to provide a compound of formula (IV)

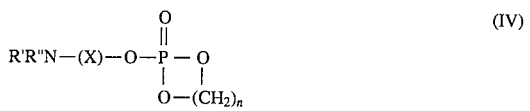

in which R',R", X and n are as hereinbefore defined, reacting the compound of formula (IV) with $NR_3$, where R is as hereinbefore defined, and, where necessary or desirable, removing all protecting groups to provide a compound of formula (I) and, if desired, converting the product thus obtained to an acid addition salt or a hydrate.

The terminal amino groups or activated amine groups, —NHZ of compounds of formula (I) and their salts and hydrates react with appropriate reactive groups at a surface which is to be rendered biocompatible. This deposits a phosphorylcholine derivative or analogue residue on the surface.

Where —NHZ is an activated amine group capable of reacting with a surface, preferably Z is:

a group B—C(O)— where B is halogen, an alkyl group, preferably containing one to four carbon atoms, unsubstituted or substituted by one or more electron withdrawing substituents, a phenyl or 5- or 6-membered heteroaromatic ring containing from 1 to 3 nitrogen atoms, optionally fused with a further phenyl ring or 5- or 6-membered heteroaromatic ring containing 1 to 3 nitrogen atoms and unsubstituted or substituted by one or more electron withdrawing substituents;

a group $B^1$—OC(O)— where $B^1$ is an alkyl group, preferably containing one or four carbon atoms, unsubstituted or substituted by one or more electron withdrawing substituents or is a phenyl or 5- or 6-membered heteroaromatic ring containing 1 to 3 nitrogen atoms, optionally fused with a further phenyl ring or 5- or 6-membered heteroaromatic ring containing 1 to 3 nitrogen atoms and unsubstituted or substituted by one or more electron withdrawing substituents; or a phenyl or 5- or 6-membered heteroaromatic ring containing 1 to 3 nitrogen atoms optionally fused with a further phenyl ring or 5- or 6-membered heteroaromatic ring containing 1 to 3 nitrogen atoms and unsubstituted or substituted by one or more electron withdrawing substituents.

Suitable electron withdrawing substituents, which may be present in the group Z, include halogen, nitro and cyano. Electron withdrawing substituents at a phenyl or heteroaromatic ring also include residues of a formula:

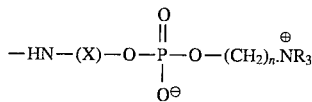

wherein R, X and n are as defined in relation to formula (I).

Where the group Z contains a heteroaromatic ring, preferably the heteroaromatic ring is an imidazole or 1,3,5-benzotriazole.

Particularly preferred compounds of formula (I) are those in which X is $-(CH_2)_a-$ and a is from 1 to 8, especially 2 to 6. Other preferred compounds are those wherein X is $-(CH_2CH_2O)_b-$ and b is from 1 to 7: those compounds in which X is $-(CH_2CH_2O)_b-$, particularly when b is higher than 7 (e.g. 8 to 10), tend to exist as mixtures of compounds with different values of b rather than as pure single compounds. The value of b may, therefore be fractional, representing an average value for the mixture of these compounds. The compounds in which X is $-CH_2(p-C_6H_4)CH_2-$, $-CH_2(p-C_6H_4)-$, $-(p-C_6H_4)CH_2-$, or $-(p-C_6H_4)-$ are preferred.

Compounds of formula (I) in which R is methyl, ethyl, n-propyl or n-butyl are also preferred, as are compounds in which all the R groups are the same.

Particularly preferred are the compounds of formula (I) which contain a phosphorylcholine moiety, ie in which each R is methyl and n is 2.

As acid addition salts of the compounds of formula (I), there may be mentioned, in particular, acid addition salts with inorganic acids such as hydrogen halides or with organic acids such as carboxylic and sulphonic acids, e.g. acetic and p-toluene sulphonic acid salts.

The coupling of the N-protected alcohols of formula (II) to the compounds of formula (III) may be performed in the presence of a base under anhydrous conditions. The reaction is typically performed at a temperature from −5° to 50° C. (preferably 10° to 30° C., e.g. 25° C.) in a dry organic solvent, e.g. acetonitrile or N,N- dimethylformamide and in the presence of an organic base, such as a tertiary amine, e.g. triethylamine or pyridine, or an inorganic base, such as an alkali metal carbonate, e.g. sodium carbonate.

The ring opening reaction may, for example, be performed in tertiary amine, e.g. trimethylamine, at a temperature from 20° to 100° C., preferably 40° to 80° C., e.g. 70° C., and in a sealed pressure vessel for 3 to 72 hours (e.g. 18 hours).

The deprotection may be performed as a separate step after or, in some cases, before the ring-opening reaction. It may also be performed at the same time as the ring-opening reaction.

The protecting groups are chosen so that they do not react with the compounds of formula (III). As examples of particular protecting groups there may be mentioned:

amides (NR' and/or NR" is an amide group), e.g. N-phthalimides;

carbamates (NR' and/or NR" is a carbamate group), e.g. 9-fluorenylmethoxycarbonylamines, or tert-butyloxycarbonylamines;

hindered secondary amines, (R' is a hindered group e.g. triphenylmethyl and R" is hydrogen); or salts, (NR'R" is a $NH_3^{\oplus}A^{\ominus}$ group). Suitable counter ions $A^{\ominus}$ are anions of organic acids, such as acetic or p-toluene sulphonic acid or inorganic acids such as hydrogen halides, e.g. hydrogen chloride.

The N-protected aminoalcohols of formula (II), may be prepared from bromoalcohols of formula (VII)

Br—(X)—OH         (VII)

or aminoalcohols of formula (VIII)

H$_2$N—(X)—OH        (VIII)

in which X is as hereinbefore defined which are commercially available or may be prepared by known methods.

In some cases however, the protected amine alcohols are themselves commercially available e.g. N-(2-hydroxyethyl)phthalimide.

In the case where the protecting group is an amide the protected amino alcohol may be prepared from either the bromoalcohol of formula (VII) or the aminoalcohol of formula (VIII) by known methods. For example if the protecting group is a phthalimide, the protected amino alcohol is obtained by reaction with an alkali metal phthalimide, e.g. potassium phthalimide. Typically the reaction with phthalimide is performed in an organic solvent such as N,N- dimethylformamide at a temperature from 70° to 110° C. e.g. 90° C. After coupling to a phosphorus compound of formula (III) and ring-opening, deprotection is performed under basic conditions (for example, in aqueous hydrazine). This gives a product of formula (I) in which Z is hydrogen which can be purified for instance by column chromatography using, for example, silica gel.

In the case where the protecting group is a carbamate, protection is afforded by reaction of an amino alcohol with, for example, a chloroformate or acid anhydride to give a carbamate. The reaction is generally performed in an organic solvent, at a temperature from 10° to 50° C. and in the presence of a base. 9-Fluorenylmethoxychloroformate, for example, reacts with amines to give 9-fluorenylmethoxycarbonylamine derivatives and di-tert-butyldicarbonate reacts with amines to give tert-butyloxycarbonylamine derivatives. Ethanolamine, for example, reacts with 9-fluorenylmethoxychloroformate under anhydrous conditions in an inert solvent such as dichloromethane, in the presence of a suitable base such as pyridine, in a temperature range such as −10° C. to 50° C., for example 10° C., to give N-9-fluorenylmethoxycarbonyl-aminoethanol. Ethanolamine reacts with di-tert-butyldicarbonate under aqueous conditions, for example, aqueous 1,4-dioxan, in the presence of a suitable base, for example sodium hydroxide, at a suitable temperature, for example −10° C. to 50° C., preferably at 0° C., to give N-tert-butyloxycarbonylaminoethanol.

The carbamate protecting groups may be removed after the coupling reaction by known methods. For example the N-9-fluorenylmethoxycarbonyl amine protecting group may be removed under basic conditions in a suitable solvent, such as acetonitrile. Suitable bases for amine deprotection include ammonia, dialkylamines such as diethylamine, trialkylamines such as trimethylamine, cyclic amines and especially cyclic secondary amines such as morpholine, piperazine, piperidine and diazabicyclic bases such as 1,5-diazabicyclo(4.3.0)non-5-ene (DBN) and 1,8-diazabicyclo(5.4.0)undec-7-ene (DBU). The deprotection conditions may be chosen such that deprotection is performed prior to ring-opening or at the same time.. The tert-butyloxycarbonyl amine protecting group may be removed using a suitable acid, for example trifluoroacetic acid or hydrochloric acid. The reaction may be performed in a suitable solvent system, for example, 1,4-dioxan/chloroform mixtures at a temperature of 0° to 50° C., for example, 21° C.

In the case where the protecting group is a hindered secondary amine the protected aminoalcohol (II) may be prepared by initial blocking of the hydroxyl function (for example, by reacting with chlorotrimethylsilane) in an organic solvent (for example, tetrahydrofuran) in the presence of an organic base (for example triethylamine). The amine function is then protected using a hindered chloroalkane (for example, chlorotriphenylmethane) in the presence of an organic base (for example, triethylamine). The hydroxyl function is then deprotected under mild conditions (for example, with methanol).

After coupling and ring opening, deprotection may be performed under acidic conditions, for example, with trifluoroacetic acid or with hydrogen chloride gas, in a non-aqueous solvent, for example, 1,4-dioxan, or chloroform. This gives the crude product which can be purified by column chromatography using, for example, silica gel.

If NR'R" is $NH_3^{\oplus}A^{\ominus}$ in the protected aminoalcohol of formula (II), it will react with the compound of formula (III) selectively via the hydroxyl group. Protected aminoalcohols in which NR'R" is $NH_3^{\oplus}A^{\ominus}$ are prepared by protonation with a suitable acid. Suitable acids include inorganic and organic acids especially p-toluenesulphonic acid which gives with, for example, ethanolamine, a crystalline p-toluenesulphonate which is soluble in a solvent suitable for the reaction with (III), for example, acetonitrile.

After coupling, these amine salts may be converted to free amines under suitable basic conditions using, for example, trimethylamine. Advantageously, the protected amine salts are ring-opened and converted to free amines in a single step using trimethylamine. In the case where the acid addition salt is desired it is not necessary to deprotect the amine group.

Alternatively the compound of formula (I) in which Z is hydrogen, may be obtained by reacting a compound of formula (V) with a compound of formula (VI) as defined above.

Generally the reaction is performed in a protic solvent, for example, water or methanol, preferably water, in which the compound (V) is dissolved and treated with a base, e.g. a tetraalkyl ammonium base, such as tetrabutyl ammonium hydroxide. The reaction mixture is subsequently treated with the halogen compound (VI). The reaction mixture is heated at elevated temperature, for example 40' to 120° C., for a period of 1 to 60 hours, preferably about 22 hours. After cooling, the pH is adjusted to e.g. 0.5 to 2.5, preferably about 1 by the addition of an acid, for example mineral acid, preferably hydrogen bromide in glacial acetic acid. The aqueous mixture is extracted with an organic solvent e.g. a chlorinated hydrocarbon such as dichloromethane. After evaporation of the aqueous layer the resulting compound of formula (I) may be obtained by chromatography on silica gel eluting with polar organic solvent mixtures e.g. ethyl acetate, acetone, methanol or water, preferably methanol.

The compounds of formula (V) and (VI) may be obtained by known methods or are commercially available.

Compounds of formula (I) in which —NHZ is an activated amine group capable of reacting with a surface may be obtained from compounds in which Z is hydrogen by conversions using known methods for the derivatisation of an amine group.

For example, compounds of formula (I) where Z is BC(O)— and B is imidazole may be prepared by treating a compound of formula (I) in which Z is hydrogen with 1,1'-carbonyldiimidazole in a solvent, such as dimethylsulphoxide optionally in the presence of a tertiary base, for example triethylamine. Generally the reaction is carried out at a temperature from −10° C. to 100° C. for example about 21° C., for 0.1 to 24 hours, for example about 1 hour.

Compounds of formula (I) where Z is a halo-1,3,5-triazine residue, e.g. a chloro-1,3,5-triazine residue, may be prepared by treating a compound of formula (I) in which Z is hydrogen with a 1,3,5-trihalotriazine, e.g. 1,3,5-trichlorotriazine. The reaction may be performed in a solvent such as aqueous acetone and, optionally in the presence of an inorganic or organic base, for example sodium hydroxide or triethylamine. The reaction is generally carried out at a temperature of from −5° to 90° C., for example, about 21° C., for 0.1 hour to 24 hours, for example about 1.5 hour. The product isolated may be a dihalotriazine derivative containing a single residue of a compound of formula (Ia), a monohalotriazine derivative containing two residues of a compound of formula (Ia) or a mixture of these di-halo and mono-halo derivatives.

If desired, the compound of formula (I) thus obtained may be converted to a hydrate or to an acid addition salt, by known methods. Conversion to acid addition salt may, for example, be performed by reaction with an inorganic acid, e.g. a hydrogen halide, or an organic acid, for instance, a carboxylic or sulphonic acid, e.g. acetic or p-toluenesulphonic acid.

Compounds of formula (I) and salts and hydrates thereof may be used to treat surfaces to render them more biocompatible. They may in particular be used to coat a surface of a substrate such as a sight correction device or another device which in use contacts a body fluid such as blood, saliva or urine, either intra- or extracorporeally.

The compounds of formula (I) in which Z is hydrogen and salts and hydrates thereof may be used to treat a surface having reactive groups activated by a prior activation step. Alternatively unactivated surfaces containing functional groups may be treated with activated compounds of formula (I), i.e, compounds in which the group —NHZ is an activated amine group.

Treatment with compounds of formula (I) and salts and hydrates thereof may be used to provide a coating treatment covalently bound to a surface. This may for example be used to provide a coating which is covalently bound to carboxyl, hydroxyl, amino or thiol group at a surface.

In one embodiment a surface containing reactive groups is treated by a process comprising the steps of
(a) activating the surface with an activating agent and
(b) treating the activated surface with a compound of formula (I) in which Z is hydrogen or a salt or hydrate thereof.

Conventional activating groups known in the art may be used. Suitable activating agents are disclosed in "Methods in Enzymology, volume 135, Immobilised Enzymes and Cells, part B", Ed K. Mosbach, Academic Press Inc, New York, 1987.

Surface hydroxyl groups may for example, be activated by conversion to sulphonate or carboxylate ester derivatives such as p-toluenesulphonate esters by reaction with p-toluenesulphonyl chloride. Other sulphonyl chlorides may be used, as may carboxylic acid derivatives optionally bearing electron withdrawing substituents so as to form activated ester derivatives. Suitable carboxylic derivatives include trifluoroacetyl chloride, trichloroacetyl chloride, 4-nitrobenzoylchloride and pentafluorobenzoyl chloride.

Surface amino groups may be activated by treatment with an acylating agent, for example 1,1'-carbonyldiimidazole. The N-acylated derivative produced may be treated directly with a compound of formula (Ia) or a salt hydrate thereof or it may be further treated to generate an isocyanate and then treated with a compound of formula (Ia) or a salt or hydrate thereof.

Surface carboxylic acid groups may be a) activated by conversion to an acid chloride anhydride or activated ester; b) treated with a carbodiimide to provide an O-acyl urea; and c) reacted with M-hydroxybenzotriazole to give a hydroxybenzotriazole ester. Reaction of such derivatives with a compound of formula (Ia) or a salt or hydrate thereof generates an amide link between the surface and the residue of the compound of formula (I).

The treatment with the compound of formula (I) or salt or hydrate thereof is generally carried out by treating the surface with a solution of the compound of formula (I) or salt or hydrate thereof, generally in an organic, or aqueous solvent or mixture of solvents e.g. mixture of aqueous and organic solvents. Suitable organic solvents include dimethyl formamide, dimethyl sulphoxide, chloroform aliphatic alcohols and acetone. Preferably an aqueous alcoholic or aqueous acetone solvent system is used. The treatment is generally carried out at a temperature from −5° to 50° C., for from 0.1 to 24 hours and at a pH from 2 to 13.

The surface of the substrate may be treated by known techniques such as dipping in or spraying with a solution of the compound of formula (I).

In one embodiment the invention provides a process for treating a polymeric surface e.g. a surface of a sight correction device, comprising the steps of
a) activating the polymeric surface to be treated with a water soluble coupling agent, and
b) treating the activated surface with a compound of formula (I) in which Z is hydrogen.

This process may be used to treat polymeric sight correction devices, such as contact lenses and intra-ocular lenses, to reduce protein deposition and improve compatibility with the eye. This process provides coating treatments which are covalently bound to the surface, e.g. a lens, and which are convenient and use economical and readily available materials. The coatings produced have good oxygen permeability and resistance to protein binding.

Conventional water soluble coupling agents, of the type known in the art may be used. Suitable coupling agents include carbodiimides, for example 1-(3-dimethylaminopropyl)-3-ethylcarbodiimide hydrochloride (IX) and 1-cyclohexyl-3-(2-morpholinoethyl)carbodiimide metho-p-toluene sulphonate (X) and isoxazolium-sulphonates, for example, 2-ethyl-5-phenylisoxazolium-3'-sulphonate (XI).

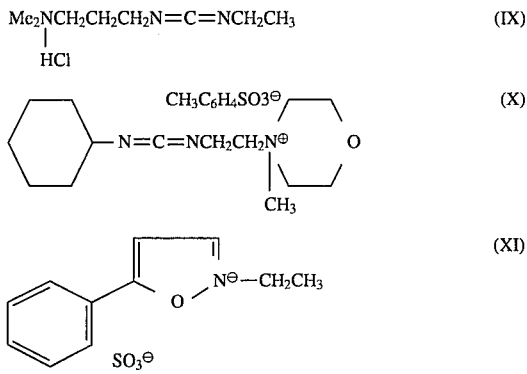

This process may result in the formation of various types of linkages between the polymeric surface and the compound of formula (I) or acid addition salt or hydrate thereof. Specifically, covalent modification of a surface carboxyl functional group with a primary amino group results in amide bond formation.

With soft contact lenses (high or low water content) the refractive index is mainly dependent on the water content of the lens material. Many surface treatments which rely on reaction with surface hydroxyl or carboxyl groups result in the derivatisation of such groups which affects the water content and may lead to a change in refractive index. This is clearly disadvantageous in the manufacture of lenses. In contrast, by using this process although polymeric carboxyl groups may be derivatised, new hydrophilic groups are introduced onto the surface of the lens by means of the reaction. The effect of the present surface treatment on refractive index is therefore minimal.

This process is typically carried out in one of three ways:

i) in two distinct stages using two treatment vessels, the lenses being washed between step (a) and step (b);

ii) in two stages but using one treatment vessel, the reagents being added sequentially at a predetermined interval; or iii) in a single stage with steps (a) and (b) carried out in the same treatment vessel and at the same time.

For methods (i) and (ii):

Step (a) is suitably conducted in aqueous medium at neutral or acidic pH in the range of from pH 3 to 7. Suitable concentrations of coupling agent in the activation solution are in the range 0.25 mM to 2.5 mM, preferably 2.5 mM to 25 mM. Activation times are typically in the range 0.5 minutes to 60 minutes preferably 0.5 minutes to 30 minutes.

Step (b) is suitably conducted in aqueous medium at neutral, alkaline or acidic pH in the range of pH 3 to 10. Suitable concentrations of compound of formula (I), or acid addition salt or hydrate thereof, are in the range of 2.5 mM to 2.5M, preferably 25 mM to 0.25M. Reaction times are typically in the range 2 hours to 16 hours, preferably 2 hours to 6 hours.

In method (i) after step (a), the lenses are washed in aqueous medium before transfer to a second treatment vessel for step (b). The wash solution is at neutral, acidic or basic pH in the range 3 to 9, preferably the same pH as the solution for step (b).

In method (ii) a solution of, the compound of formula (I) or acid addition salt or hydrate thereof, is added to the reaction treatment vessel for step (a), as defined above, without further modification.

In method (iii) reagents necessary for boths steps (a) and (b) are added simultaneously or the sight correction device is first swollen with a solution of a compound of formula (I) or an acid addition salt or hydrate thereof and then a solution of coupling agent is added. Suitable media, pH, times and concentrations are as defined above.

For all three treatment methods the reactions are preferably conducted at 0° C. or above provided that the temperature does not damage the chemical structure or physical properties of the lens being treated. Preferably therefore the reaction is conducted at up to 50° C., more preferably at from 4° C. to 30° C.

Following the treatment of the polymeric surface the device may be washed to remove the unreacted reagents, for instance using borate buffered saline, or other physiologically acceptable buffer.

The process may be carried out in a gel matrix modification regulating medium. When modification of the entire polymer matrix is desired, the polymeric hydrogel is swollen in aqueous solutions containing a suitable swelling agent such as urea or guanidine hydrochloride. Suitable concentrations of, for example, the urea solution are 1M to 8M, more preferably 6M to 8M. Solutions of the reagents can be prepared in urea solutions at concentrations and pH, as defined above, and used to achieve the process of the invention.

According to a further embodiment, a compound of formula (I) in which —NHZ is an activated amine group or a salt or hydrate thereof may be used to treat a surface without prior activation of the surface functional groups.

For example a compound of formula (I) where Z is B—C(O)— and B is a heteroaromatic group such as imidazole may be used to treat a surface bearing hydroxyl group. For example the surface may be treated with an aqueous solution at a pH value in the range of 5 to 14, for example about 9.5. This procedure generates a carbamate linkage between the surface and the residue of the compound of formula (I).

A compound of formula (I) where Z is B—C(O)— and B is a heteroaromatic group such as imidazole or a salt or hydrate thereof may also be used to treat a surface bearing primary or secondary amino groups. The reaction may be performed under aqueous or non-aqueous conditions, at a temperature from 0° C. to 100° C., for example 20° to 25° C. and for 0.5 to 24 hours, e.g. about 2 hours, at a pH from 2 to 14, for example 8.5. This generates a urea linkage between the surface and the residue of the compound of formula (I).

A compound of formula (I) where Z is 1,3,5-triazine or a salt or hydrate thereof may be used to treat a surface bearing primary or secondary amino groups. The reaction may be performed under aqueous or non-aqueous conditions, for example at temperature from 0° to 100° C., for example 20° to 25° C., at a pH from 2 to 14, for example about 5.5 and for 0.5 to 24 hours, for example about 1 hour. This generates a covalent attachment from the surface to the residue of the compound (I) via the triazine residue.

Where necessary the surface of the substrate to be treated may be functionalised prior to treatment. For surfaces which do not have functional groups such as hydroxyl, thiol, carboxyl or amino groups, it is necessary to introduce these groups at the surface before treatment with the compound of formula (I) or salt or hydrate thereof. This can be effected by known etching or derivatising techniques, such as plasma polymerisation, which introduces the appropriate surface functionality (see for example "Chemical Reactions of Polymers" Ed. E. M. Fettes, 1964, Interscience, London).

Materials having surfaces treated according to the present invention can be used as a construction material for implants or prostheses of the human or animal body, particularly where these implants or prostheses are to come into direct physical contact with blood and where biocompatibility and particularly haemocompatibility are required e.g. in heart valves. They can also be used in the construction of separation membranes and other devices that are to be brought into contact with blood or protein solutions, such as other body fluids on an extra-corporeal basis, for example in heart-lung machines or artificial kidneys.

When the compounds of formula (I) or salts or hydrates thereof are used to treat the surface of a material which is then used in the construction of a finished device, it may be necessary to take precautionary steps to ensure that the treated surface is not damaged and the effectiveness of the treatment reduced before the finished device is produced.

In addition, the compounds of formula (I) and salts and hydrates thereof can be used to treat finished implants, prostheses, membranes catheters, contact lenses and other devices which are treated with a compound of formula (I) or salt or hydrate thereof to impart biocompatibility to the article.

The present invention will now be further illustrated with reference to the following examples:

EXAMPLES 1 TO 5

Preparation of
2-[(2-Aminoethoxyhydroxyphosphinyl)oxy]-N, N,N-trimethylethanaminium hydroxide, inner salt

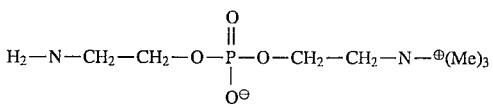

EXAMPLE 1 (Salt protecting group)

Ethanolamine p-toluenesulphonate (10.0 g, 39.8 mmol was dissolved in dry acetonitrile (500 ml) at 60° C. The solution was cooled to 30° C. when pyridine (3.15 g, 39.8 mmol) was added. A solution of 2-chloro-2-oxo-1,3,2-dioxaphospholane (5.68 g, 39.8 mmol) in dry acetonitrile (5 ml) was then added over 10 minutes. The mixture was stirred at ambient temperature for 4 hours and then the acetonitrile evaporated in vacuo to give 2-(2-aminoethoxy)-2-oxo-1,3,2-dioxaphospholane as a viscous oil.

2-(2-aminoethoxy)-2-oxo-1,3,2-dioxaphospholane was dissolved in acetonitrile (20 ml) and added to trimethylamine (14.3 ml) in a glass pressure bottle stored in liquid nitrogen. The pressure bottle was closed, allowed to warm to ambient temperature over 0.5 hour and was then warmed to 60° C. for 16 hours. A pale yellow gum was deposited during this time. Excess trimethylamine was bubbled off and the supernatant decanted. The gum was dissolved in methanol, preabsorbed onto silica gel and purified by chromatography on silica gel eluting with methanol and methanol/25% aqueous ammonia mixtures. 2-[(2-Aminoethoxyhydroxyphosphinyl)oxy]-N,N,N-trimethylethanaminium hydroxide, inner salt was obtained as a pale yellow foam.

EXAMPLE 2 (Carbamate protecting group)

2-Aminoethanol (1.2 g, 19.7 mmol) in dry dichloromethane (5 ml) was added dropwise to a solution of 9-fluorenylmethylchloroformate (5.0 g, 19.3 mmol) together with pyridine (1.5 g, 19.4 mmol). The mixture was stirred for a total of 1.25 hours then diluted with dichloromethane (50 ml), washed with water (25 ml), a saturated solution of ammonium chloride (25 ml), the organic phase was separated dried over anhydrous magnesium sulphate, filtered and the filtrate evaporated in vacuo to give a white solid. This material was crystallised from dichloromethane to give 2-(9-fluorenylmethoxycarbonyl)aminoethanol.

I.R. max (KBr) 3475, 3355, 1674, 1543, 1276, 1250, 1070, 762, 741 cm$^{-1}$.

$^1$Hnmr (60 MH$_z$) (CDCl$_3$) δ 7.8-7.2 (8H,complex), 4.5-4.1 (3H, complex), 3.8-3.5, (2H,m) and 3.4-3.1 (2H,m) ppm.

2-Chloro-2-oxo-1,3,2-dioxaphospholane (1.4 g, 9.9 mmol) in dry dichloromethane (5 ml) was cooled to 0° C. under a nitrogen atmosphere as pyridine (0.8 ml) and a solution of 2-(9-fluorenylmethoxycarbonyl)aminoethanol (2.8 g) in dry dichloromethane (80 ml) and dry acetonitrile (20 ml) were added separately but simultaneously, ensuring the presence of a slight excess of base during the addition. The mixture was allowed to warm to ambient temperature and was stirred for 2 hours. The mixture was then evaporated in vacuo and the crude reaction product dissolved in dry acetonitrile (10 ml) and added to trimethylamine (3.3 ml) in a glass pressure bottle stored in liquid nitrogen. The pressure bottle was sealed, allowed to warm to ambient temperature over 0.5 hour and was then warmed to 60° C. for a total of 60 hours. The mixture was cooled, excess trimethylamine bubbled off and the supernatent liquid was decanted. The residual gum was dissolved in methanol (20 ml), filtered and evaporated in vacuo.

The crude product was purified using column chromatography on silica gel eluting with methanol and methanol/25% aqueous ammonia mixtures to give 2-[(2-aminoethoxyhydroxyphosphinyl)oxy]-N,N,N-trimethylethanaminium hydroxide, inner salt as a pale yellow gum.

EXAMPLE 3 (Amide protecting group)

To a solution of 2-chloro-2-oxo-1,3,2-dioxaphospholane (30 g, 211 mmol) in dry acetonitrile (400 ml) containing anhydrous sodium carbonate (270 mg) was added N-(2-hydroxyethyl)phthalimide (40.3 g, 211 mmol). Anhydrous chloroform was added until all the organic material was solubilised, after which the mixture was stirred at room temperature for two hours. The solvents were removed under reduced pressure and the residue was dissolved in dry acetonitrile (100 ml) which was added to frozen trimethylamine (37.4 g, 633 mmol) in a pressure vessel at liquid nitrogen temperature. The vessel was sealed and the mixture heated at 60° C. for 40 hours. The mixture was cooled and filtered. The hydroscopic solid was washed with dry acetonitrile and dissolved in water (200 ml). Hydrazine (15 ml, 15.3 g, 478 mmol) was added and stirring maintained at ambient temperature for two hours when concentrated hydrochloric acid was added until the pH reached 1.5. The resulting white solid was removed by filtration and washed with water. The filtrate and washings were combined and the pH adjusted to 9.0 with ammonium hydroxide (40% solution). The water was evaporated under reduced pressure leaving a white solid which was heated to 150° C. for three hours in a sublimation apparatus. The residue was crystallised from water to give 2-[(2-aminoethoxyhydroxyphosphinyl)oxy]-N,N,N-trimethylethanaminium hydroxide, inner salt.

EXAMPLE 4 (Hindered secondary amine protecting group)

Ethanolamine (5 g, 82 mmol) and triethylamine (11.4 ml, 8.28 g, 82 mmol) were dissolved in dry tetrahydrofuran (50 ml). Chlorotrimethylsilane (10.4 ml, 8.90 g, 82 mmol) was added over five minutes and the mixture was stirred for 30 minutes. The white solid was removed by filtration and washed with dry tetrahydrofuran. The combined filtrate and washings were stirred and triethylamine (11.4 ml, 8.28 g, 82 mmol) was added followed by chlorotriphenylmethane (22.8 g, 82 mmol). The mixture was stirred at ambient temperature for two hours, when it was filtered and the filtrate cooled to 0° C. for 30 minutes. Following a further filtration the liquors were stirred with methanol (60 ml) for fifteen minutes. The solvent was removed under vacuum and the residue crystallised from hot ethyl acetate. The resulting white solid was dried under vacuum at room temperature for 16 hours before triturating successively with diethyl ether (twice) and acetone (twice). The residue was heated with boiling acetone (700 ml) for ten minutes before the solid was collected by filtration, washed with cold acetone and dried under vacuum for four hours to give N-(triphenylmethyl) ethanolamine.

1H-NMR, (60 MH$_z$),(CD$_3$OD),δ7.4 (15H,s), 3.65 (2H,q) and 2.85 (2H,m) ppm

N-(Triphenylmethyl)ethanolamine (5 g, 16.5 mmol) was taken in dry N,N-dimethylformamide (100 ml) and dry acetonitrile (50 ml) and anhydrous sodium carbonate (300 mg) was added. 2-Chloro-2-oxo-1,3,2-dioxaphospholane (2.35 g, 16.5 mmol) was added, followed by triethylamine until all the organic compounds were in solution. The mixture was stirred under nitrogen for three hours, filtered under nitrogen and the filtrate carefully added to frozen trimethylamine (7.5 ml) in a pressure vessel. After sealing the reaction vessel was heated at 70° C. for 40 hours. The mixture was cooled, excess trimethylamine was bubbled off and the solvent was then evaporated under reduced pressure and the residue partitioned between water (500 ml) and chloroform (500 ml). The organic layer was discarded and the aqueous layer re-extracted with chloroform. The aqueous layer was evaporated under reduced pressure (at 65° C.) to leave a coloured gum which was treated with acetone (500 ml). The solvent was decanted and the resulting solid was dissolved in methanol (30 ml) and treated with hydrochloric acid (0.5M) until pH 1.5 was reached. After stirring for an hour the solvents were evaporated under reduced pressure and the residue was treated with benzene (20 ml) and evaporated in vacuo. The gum was then treated with trifluoroacetic acid (5 ml) and stirred at ambient temperature for five minutes. The solvent was evaporated under reduced pressure and the residue was treated with benzene (20 ml) and evaporated in vacuo. Water (25 ml) was added and the resulting solid was recovered by filtration and washed with water (10 ml). The combined filtrate and washings were evaporated under reduced pressure and the residue chromatographed on silica gel, eluting with methanol. 2-[(2-Aminoethoxyhydroxyphosphinyl)oxy]-N,N,N-trimethylethanaminium hydroxide, inner salt was isolated, as the trifluoroacetic acid salt, after evaporation of the relevant fractions.

EXAMPLE 5 (Carbamate protecting group)

To a solution of N-(tert-butoxycarbonyl)ethanolamine (5 g, 31 mmol) in dry acetonitrile (100 ml) was added anhydrous sodium carbonate (300 mg) and 2-chloro-2-oxo-1,3,2-dioxapholane (4.42 g, 31 mmol). The mixture was stirred under nitrogen for two hours at ambient temperature. After filtration the mixture was carefully added to frozen anhydrous trimethylamine (20 ml) in a pressure vessel. The reaction vessel was sealed and heated at 70° C. for 48 hours. The excess trimethylamine was removed by bubbling the gas through dilute hydrochloric acid (0.1M). The solvent was evaporated in vacuo and the residue dissolved in methanol and chromatographed on silica gel. The fractions containing the product were combined, evaporated and treated with benzene (20 ml) and evaporated in vacuo.

To the residue trifluoroacetic acid (20 ml, 29.6 g, 260 mmol) was added and left at ambient temperature for 30 minutes. Methanol (100 ml) was added and the mixture evaporated under reduced pressure. Ethanol (100 ml) was added and the procedure repeated. Acetone (100 ml) was added to the residue and the resulting sticky solid was isolated by decanting the solvent. The residue was twice treated with benzene (100 ml), evaporated in vacuo, to give 2-[(2-aminoethoxyhydroxyphosphinyl)oxy]-N,N,N-trimethylethanaminium hydroxide, inner salt as the trifluoroacetic acid salt.

1Hnmr (300 MHz) (CD$_3$OD) δ 4.69 (s,HOD), 4.30 (2H, m), 4.01 (4H,m), 3.66 (2H,m) 3.23 (9H, s) and 3.05 (2H,m) ppm Mass spectrum FAB (3-nitrobenzyl alcohol matrix) observed mass 227.1 (MH$^+$). Calculated mass for C$_7$H$_{20}$N$_2$O$_4$P 227.

EXAMPLES 6 AND 7

Preparation of
2-[(6-Aminohexyloxyhydroxyphosphinyl)oxy]-N, N,N-trimethylethanaminium hydroxide, inner salt

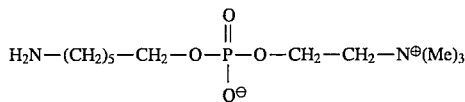

EXAMPLE 6 (Amide protecting group)

6-Bromohexan-1-ol (8 g, 44 mmol) and potassium phthalimide (16.4 g, 88 mmol) were heated at 90° C. for two hours in dry N,N-dimethylformamide (50 ml). The mixture was cooled and partitioned between chloroform (150 ml) and water (150 ml). The organic layer washed with water (2×150 ml), dried over anhydrous magnesium sulphate, filtered, and the filtrate evaporated under reduced pressure to give a yellow liquid. The liquid was left at 4° C. for 72 hours before repartitioning between ethyl acetate (150 ml) and water (150 ml). The organic layer was washed with water (2×150 ml), dried over anhydrous magnesium sulphate, filtered, and the filtrate evaporated under reduced pressure. Diethyl ether was added and following cooling the solid was removed by filtration. The process was repeated and the liquors were evaporated to give N-(6-hydroxyhexyl)-phthalimide. 1H-NMR: (60 MH$_z$) (CDCl$_3$), δ 7.7 (4H,s), 3.6 (5H,m) and 1.4 (8H,m) ppm To a solution of 2-chloro-2-oxo-1,3,2-dioxaphospholane (2.9 g, 20.2 mmol) in dry acetonitrile (150 ml) was added anhydrous sodium carbonate (200 mg, 1.9 mmol) and N-(6-hydroxyhexyl)phthalimide (5 g, 20.2 mmol). The mixture was stirred under nitrogen for 90 minutes. The mixture was evaporated under reduced pressure to a smaller volume (40 ml) which was slowly added to frozen (liquid nitrogen) anhydrous trimethylamine (9 ml) in a pressure vessel. The vessel was sealed and heated at 60° C. for eighteen hours. The solution was cooled, excess trimethylamine was bubbled off, the solution filtered to remove solids and the filtrate evaporated to dryness under reduced pressure. The crude compound was chromatographed on silica gel eluting with methanol. 2-[(6-N-phthalimidoaminohexyloxy-hydroxyphosphinyl)oxy]-N,N,N-trimethylethanaminium hydroxide, inner salt was isolated by evaporation of the product containing fractions 1H-NMR (60 MH$_z$) (CD$_3$OD) δ 7.7 (4H,s), 4.7-3.0 (17H,m) and 1.4 (8H,m) ppm Tlc: Silica, eluent methanol: water, 9:1, RF=0.35 (UV, sprays with molybdenum blue and Dragendorff's reagent).

2-[(6-N-Phthalimidoamino)hexyloxyhydroxyphosphinyl)oxy]-N-N-N-trimethylenthanaminium hydroxide, inner salt (4.36 g, 10.6 mmol) was dissolved in water (25 ml). Hydrazine (18 ml, 18.4 g, 573 mmol) was added and the mixture stirred to ambient temperature for one hour. The mixture was subjected to a vacuum (at temperature less than 40° C.) for five minutes before the pH of the solution was adjusted to 1.5 with concentrated hydrochloric acid. The mixture was stirred for five minutes and then filtered to remove the solid. The filter cake was washed with water (x2) and the filtrate and washings were combined and evaporated under reduced pressure. The residue was azeotroped with benzene (x2) and dried under vacuum for 16 hours. The residue was stirred with absolute alcohol (100 ml) for five minutes. The ethanolic solution was removed and the residue retreated with ethanol (2×100 ml). The combined solutions were evaporated to dryness and the crude compound purified by silica chromatography eluting with methanol. The product was isolated after evaporation of the relevant fractions and treated with benzene (20 ml) and evaporated in vacuo to give 2-[6-aminohexyloxyhydroxyphosphinyl)oxy]-N,N,N-trimethylethanaminium hydroxide, inner salt as a white hydroscopic gum.

EXAMPLE 7 (Carbamate protecting group)

To a solution of aminohexan-6-ol (5.9 g, 0.05 mol) in 1,4-dioxan (150 ml) was added an aqueous solution of sodium hydroxide (1.0M, 90 ml) and water (90 ml). The mixture was stirred at 0° C. when di-tert-butyldicarbonate (11.16 g, 0.05 mmol) was added. The mixture was stirred for two hours while allowing the temperature to return to ambient. The mixture was evaporated under vacuum to remove the organic solvents before it was cooled to 0° C. and the resulting aqueous phase extracted with ethyl acetate. (3×150 ml). The combined organic extracts where dried over anhydrous magnesium sulphate, filtered and evaporated to dryness under reduced pressure. The crude product was chromatographed on silica gel, eluting with methanol. The relevant fractions were combined and evaporated to dryness under reduced pressure to give N-(tert-butoxycarbonyl)aminohexan-6-ol.

1H-NMR (60 MH$_z$) (CDCl$_3$) δ 4.95 (1H,s), 3.6 (2H,m), 3.1 (2H,m) and 1.45 (17H,m) ppm.

N-(tert-butoxycarbonyl)aminohexan-6-ol (7.5 g, 34.5 mmol) was dissolved in dry acetonitrile (150 ml) and anhydrous sodium carbonate (400 mg) was added. 2-Chloro-2-oxo-1,3,2-dioxaphospholane (4.92 g, 34.5 mmol) was added and the mixture stirred under nitrogen for 45 minutes. The solvent was partially evaporated to a volume of about 40 ml which was added to frozen anhydrous trimethylamine (10 ml, liquid nitrogen temperatures). The mixture was heated in a sealed reaction vessel for 18 hours at 70° C. The vessel was cooled, excess trimethylamine was bubbled off and the suspension filtered. The filtrate was evaporated to dryness under reduced pressure.

The crude material was purified on silica gel eluting with chloroform and then methanol to give 2-[(6-(N-tert-butoxycarbonylamino)hexyloxyhydroxyphosphinyl)oxy]-N,N,N-triemethylethanaminium hydroxide, inner salt. 1H-NMR (60 MH$_z$) (CD$_3$OD) δ 4.0-2.6 (17H,m) and 1.1 (17H,m) ppm.

2-[(6-(N-tert-Butoxycarbonylamino)hexyloxyhydroxyphosphinyl)oxy]-N,N,N-triemethylethanaminium hydroxide, inner salt (7.33 g, 19.2 mmol) was dissolved in a mixture of dry 1,4-dioxan (150 ml) and dry chloroform (75 ml). Hydrogen chloride gas was bubbled through the mixture until a white gum had been deposited. The solvent was evaporated under reduced pressure and the residue triturated with dry chloroform prior to re-evaporation. The mixture was dissolved in methanol, re-evaporated under reduced pressure and dried under vacuum for two hours to give 2-[6-aminohexyloxyhydroxyphosphinyl)oxy]-N,N,N-trimethylethanaminium hydroxide, inner salt as the hydrogen chloride salt.

1H-NMR (300 MH$_z$) (CD$_3$OD) δ 4.26 (2H,m), 3.90 (2H,q), 3.64 (2H,t), 3.23 (9H,s) 2.92 (2H,t), 1.67 (4H,m) and 1.46 (4H,m) ppm.

Mass spectrum FAB (3-nitrobenzyl alcohol matrix) observed mass 283.1 (MH$^+$). Calculated mass for $C_{11}H_{20}N_2O_4P$ 283.

EXAMPLE 8

2-[(2-Aminoethoxyhydroxyphosphinyl)oxy]-N-N-N-trimethylethanaminium hydroxide, inner salt Aminoethyl dihydrogen phosphate (5 g, 35.4 mmol) was dissolved in water (25 ml). An aqueous solution of tetrabutylammonium hydroxide (40%, 23 g, 35.4 mmols) was added and the mixture stirred at ambient temperature for five minutes. A solution of bromoethyltrimethylammonium bromide (8.74 g, 35.4 mmol) in water (15 ml) was added and the mixture was heated to 70° C. for two hours. The temperature was increased to 100° C. and further tetrabutylammonium hydroxide solution (40%, 12 g, 18.5 mmol) was added. These conditions were maintained for 20 hours when the reaction mixture was allowed to cool to ambient temperature, acidified with hydrobromic acid in acetic acid until pH1 was reached and extracted with dichloromethane (3×100 ml). The aqueous layer was evaporated to a colourless gum which was dissolved in methanol (50 ml) and cooled to 0° C. for one hour. A white solid was removed by filtration. This procedure was repeated twice before the solution was applied to a column of silica gel (120 g) made up in ethyl acetate. The column was eluted with methanol and product containing fractions were combined and evaporated to give 2-[(2-Aminoethoxyhydroxyphosphinyl)oxy]-N-N-N-trimethylethanaminium hydroxide, inner salt.

EXAMPLE 9

2-[(2-Imidazolecarboxylaminoethoxyhydroxyphosphinyl)oxy]-N,N,N-trimethylethanaminium hydroxide, inner salt.

2-[(2-Aminoethoxyhydroxyphosphinyl)oxy]-N,N,N-trimethylethanaminium hydroxide, inner salt (0.32 g, 1.4 mmol) was added, portion-wise to a mixture of dry dimethylsulphoxide (3 ml), trimethylamine (0.4 ml, 2 eq) and 1,1'-carbonyldiimidazole (0.46 g, 2 eq). The phosphoryl choline derivative dissolved to give a clear solution after a few minutes of stirring at room temperature. After a total of 1 hour the mixture was dripped into dry acetone (200 ml). After 0.25 hour the supernatent liquid was decanted and the gummy residue washed with acetone and dried in a stream of dry nitrogen gas.

$^1$Hnmr (60 Mhz) CD$_3$OD δ 8.1(1H,bs), 7.5 (1H, bs), 6.9 (1H, bs) 4.3-3.5 (4H, complex), 3.5-3.2 (4H, complex) and 3.1 (9H,s) ppm.

Mass spectrum FAB (3-nitrobenzyl alcohol matrix) observed mass 321 (MH+) and 253 (MH+-imidazole). Calculated mass for C$_{11}$H$_2$N$_4$O$_5$P 320.

EXAMPLE 10

Reaction of 2,4,6-trichloro-1,3,5-triazine with 2-[(2-aminoethoxyhydroxyphosphinyl)oxy]N,N,N-trimethylethanaminium hydroxide, inner salt 2,4,6-trichloro-1,3,5-triazine (0.18 g 1 mmol) in acetone (3 ml) was stirred at 0° C. as sodium hydroxide (0.04 g, 1 eq) and 2-[(2-aminoethoxyhydroxyphosphinyl)oxy]-N,N,N-trimethylethanaminium hydroxide, inner salt (0.23 g, 1 mmol) in water (1 ml) were added.

More acetone (2 ml) was added and the solution was stirred for a total of 1.5 hour at room temperature. The mixture was filtered and the filtrate evaporated under reduced pressure. The filtrate was washed with acetone (5 ml) and dried in a stream of dry nitrogen gas.

This reaction produces a mixture of 2,4-dichloro-6[2[(2-aminoethoxyhydroxyphosphinyl)oxy]N,N,N-trimethylethanaminium hydroxide inner salt]-1,3,5-triazine, in which one of the chlorine atoms of the triazine, starting material has been replaced by a residue of the 2-[(2-aminoethoxyhydroxyphosphinyl)oxy]N,N,N-trimethylethanaminium hydroxide inner salt and 2-chloro-4,6[di-2[(2-aminoethoxyhydroxyphosphinyl)oxy]N,N,N-trimethylethanaminium hydroxide inner salt]-1,3,5-triazine, in which two of the chlorine atoms of the triazine have been so replaced. These products may be separated or they may be used as a mixture. Mass spectrum FAB (3-nitrobenzyl alcohol matrix) observed mass 564 calculated mass for C$_{17}$H$_{36}$N$_7$O$_8$P$_2$Cl 563.5

EXAMPLE 11

Example reaction between a polymeric surface bearing carboxylic acid groups and a compound of formula (I)

The surface organic acid group first reacts with, a coupling agent, compound (IX), which activates the surface:

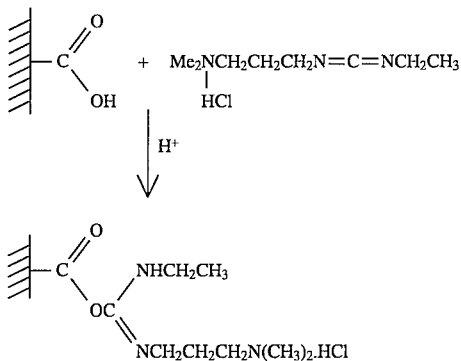

This activated intermediate reacts further, for example with 2-((2-aminoethoxyhydroxyphosphinyl)oxy)-N,N,N-trimethylethaminium hydroxide inner salt

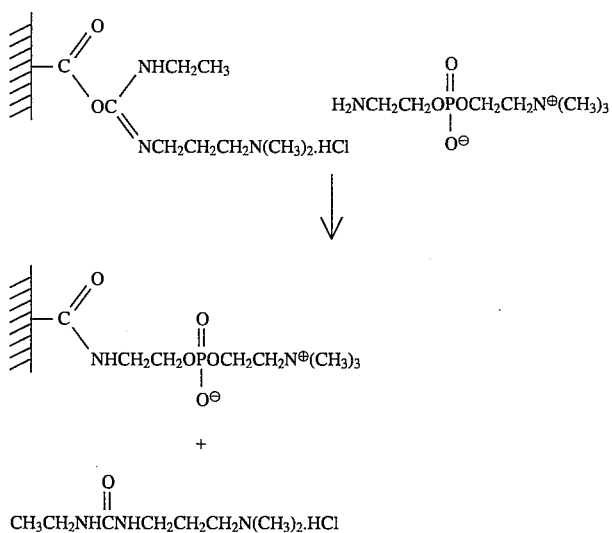

EXAMPLE 12

Acrylic acid layers were put down on stainless steel and polyimide surfaces by plasma polymerisation following surface activation using oxygen plasma. Samples (1 cm$^2$) were prepared by reaction of a compound of formula (Ia) with the acrylic acid subbed layers using dimethylaminopropyl-ethyl carbodiimide at pH 4.5 for 1 hour followed by a further 1 hour at pH 10. The reaction pH was adjusted using HCl and NaOH. At the end of this time the samples were removed from the reaction solution and washed with water to remove any unreacted materials from the surface.

We claim:

1. A process for the preparation of a compound of formula (Ia):

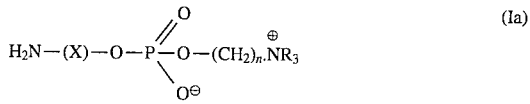

in which the groups R are the same or different and each is a straight or branched $C_1$–$C_4$ alkyl group;

n is from 2 to 4; and

X is selected from the group consisting of straight and branched $C_{1-20}$ alkylene groups, groups of formula —$(CH_2CH_2O)_b$—, and groups of formula —$(CH_2)_c$—Ar—$(CH_2)_d$— where b is from 1 to 20, c and d are the same or different and each is from 0 to 5, Ar is a phenyl ring and the groups $(CH_2)_c$ and $(CH_2)_d$ are positioned on the phenyl ring Ar at the para- or meta- positions, and in which Ar is optionally substituted by one or more $C_1$–$C_4$ alkyl groups, or an acid addition salt thereof or a hydrate thereof, which process comprises:

(a) reacting a compound of formula (II):

R'R"N—(X)—OH  (II)

in which R' is a protecting group such that NR' is selected from the group consisting of amide, carbamate and hindered secondary amine groups and R" is a protecting group such that NR" is selected from the group consisting of an amide and a carbamate group or R" is hydrogen, or R' and R" together form a protecting group, such that R'R"N is an imide, or NR'R" is $NH_3^\oplus A^\ominus$ in which $A^\ominus$ is an anion selected from the group consisting of acetate, para-toluene-sulphonate and halide ions, with a compound of formula (III):

in which n is from 2 to 4 and Hal is halogen, to provide a compound of formula (IV):

in which R', R" and X are as hereinbefore defined and n is from 2 to 4, reacting the compound of formula (IV) with $NR_3$, where R is as hereinbefore defined and removing all protecting groups to provide a compound of formula (Ia).

2. A process according to claim 1 in which NR'R" together are a phthalimide, a group $NH_3^\oplus A^\ominus$, or R' is selected from the group consisting of 9-fluoroenylmethoxycarbonyl, a tert-butyloxycarbonyl and a triphenylmethyl group.

3. A process according to claim 1 wherein a compound of formula (IV) in which n is 2 is reacted with a compound $NR_3$ in which each R is methyl.

4. A process according to claim 1 in which X is a straight chain alkylene of the formula —$(CH_2)_a$—, where a is from 1 to 8 or of formula —$(CH_2CH_2O)_b$— where b is from 1 to 7 or of formula —$(CH_2)_c$—Ar—$(CH_2)_d$—, wherein c is 0 or 1 and d is 0 or 1.

5. A process for the preparation of a compound of formula (I) or a salt or hydrate thereof:

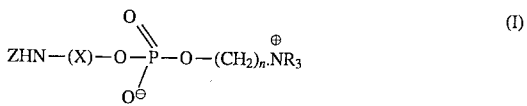

in which the groups R are the same or different and each is a straight or branched $C_1$–$C_4$ alkyl group;

n is from 2 to 6; and

X is selected from the group consisting of straight and branched $C_{1-20}$ alkylene groups, groups of formula —$(CH_2CH_2O)_b$— where b is from 1 to 20, and groups of formula —$(CH_2)_c$—Ar—$(CH_2)_d$— where c and d are the same or different and each is from 0 to 5, Ar is a phenyl ring and the groups $(CH_2)_c$ and $(CH_2)_d$ are positioned on the phenyl ring Ar at the para- or meta- positions, and in which Ar is optionally substituted by one or more $C_1$–$C_4$ alkyl groups; and Z is selected from the group consisting of:

B—C(O)— where B is imidazole; and a halo-1,3,5-triazine residue;

by treating a compound of the formula (Ia)

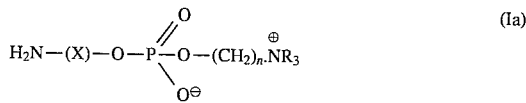

in which R, n and X are as defined above, where Z is a BC(O)— and B is imadazole, with 1,1'-carbonyldiimidazole in a solvent, or where Z is a halo-1,3,5-triazine residue, with 1,3,5-trihalotriazine in a solvent.

6. A compound of formula (Ia):

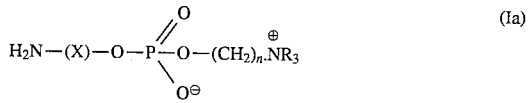

in which the groups R are the same or different and each is a straight or branched $C_1$–$C_4$ alkyl group;

n is from 2 to 6; and

X is selected from the group consisting of groups of formula —$(CH_2CH_2O)_b$— where b is from 1 to 20, and groups of formula —$(CH_2)_c$—Ar—$(CH_2)_d$— where c and d are the same or different and each is from 0 to 5, Ar is a phenyl ring and the groups $(CH_2)_c$ and $(CH_2)_d$ are positioned on the phenyl ring Ar at the para- or meta- positions, and in which Ar is optionally substituted by one or more $C_1$–$C_4$ alkyl groups, or an acid addition salt thereof or a hydrate thereof.

7. A compound of formula (I):

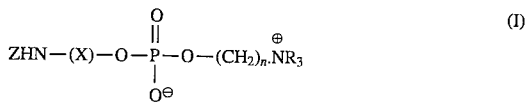

in which Z is selected from the group consisting of:

groups B—C(O)— where B is selected from the group consisting of halogen atoms, alkyl groups, unsubstituted or substituted by one or more electron withdrawing substituents, phenyl, and 5- and 6-membered heteroaromatic rings containing 1 to 3 nitrogen atoms, optionally fused with a further phenyl ring or 5- or 6-membered heteroaromatic ring containing 1 to 3 nitrogen atoms and unsubstituted or substituted by one or more electron withdrawing substituents;

groups $B^1$—OC(O)— where $B^1$ is selected from the group consisting of alkyl groups, unsubstituted or substituted by one or more electron withdrawing substituents, phenyl and 5- and 6-membered heteroaromatic rings containing 1 to 3 nitrogen atoms, optionally fused with a further phenyl ring or 5- or 6-membered heteroaromatic ring containing 1 to 3 nitrogen atoms and unsubstituted or substituted by one or more electron withdrawing substituents; and phenyl and 5- or 6-membered heteroaromatic rings containing 1 to 3 nitrogen atoms optionally fused with a further phenyl ring or 5- or 6-membered heteroaromatic ring containing 1 to 3 nitrogen atoms and unsubstituted or substituted by one or more electron withdrawing substituents;

the groups R are the same or different and each is a straight or branched $C_1$–$C_4$ alkyl group;

n is from 2 to 6; and

X is selected from the group consisting of straight and branched $C_{1-20}$ alkylene groups, groups of formula —$(CH_2CH_2O)_b$— where b is from 1 to 20, and groups of formula —$(CH_2)_c$—Ar—$(CH_2)_d$— where c and d are the same or different and each is from 0 to 5, Ar is a phenyl ring and the groups $(CH_2)_c$ and $(CH_2)_d$ are positioned on the phenyl ring Ar at the para- or meta-positions, and in which Ar is optionally substituted by one or more $C_1$–$C_4$ alkyl groups; or an acid addition salt thereof or a hydrate thereof.

8. A compound according to claim 7 in which Z is an imidazolyl or 1,3,5-triazinyl group.

9. A compound according to claim 6, in which each group R is methyl and n is 2.

10. A process for treating a surface which comprises contacting the surface with a compound of formula (I):

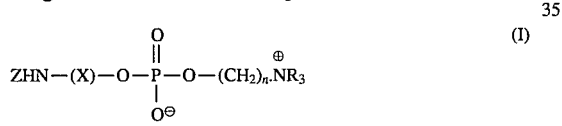

in which Z is selected from the group consisting of:

groups B—C(O)— where B is selected from the group consisting of halogen atoms, alkyl groups, unsubstituted or substituted by one or more electron withdrawing substituents, phenyl, and 5- and 6-membered heteroaromatic rings containing 1 to 3 nitrogen atoms, optionally fused with a further phenyl ring or 5- or 6-membered heteroaromatic ring containing 1 to 3 nitrogen atoms and unsubstituted or substituted by one or more electron withdrawing substituents;

groups $B^1$—OC(O)— where $B^1$ is selected from the group consisting of alkyl groups, unsubstituted or substituted by one or more electron withdrawing substituents, phenyl and 5- and 6-membered heteroaromatic rings containing 1 to 3 nitrogen atoms, optionally fused with a further phenyl ring or 5- or 6-membered heteroaromatic ring containing 1 to 3 nitrogen atoms and unsubstituted or substituted by one or more electron withdrawing substituents; and phenyl and 5- or 6-membered heteroaromatic rings containing 1 to 3 nitrogen atoms optionally fused with a further phenyl ring or 5- or 6-membered heteroaromatic ring containing 1 to 3 nitrogen atoms and unsubstituted or substituted by one or more electron withdrawing substituents;

the groups R are the same or different and each is a straight or branched $C_1$–$C_4$ alkyl group;

n is from 2 to 6; and

X is selected from the group consisting of straight and branched $C_{1-20}$ alkylene groups, groups of formula —$(CH_2CH_2O)_b$— where b is from 1 to 20, and groups of formula —$(CH_2)_c$—Ar—$(CH_2)_d$— where c and d are the same or different and each is from 0 to 5, Ar is a phenyl ring and the groups $(CH_2)_c$ and $(CH_2)_d$ are positioned on the phenyl ring Ar at the para- or meta-positions, and in which Ar is optionally substituted by one or more $C_1$–$C_4$ alkyl groups, or an acid addition salt thereof or a hydrate thereof, thereby reacting the group —NHZ with the surface.

11. A process for treating a surface which comprises:

a) activating the surface by treatment with a water-soluble activating agent in an aqueous environment, and b) treating the activated surface with a compound of formula (Ia) as defined below or a salt or hydrate thereof:

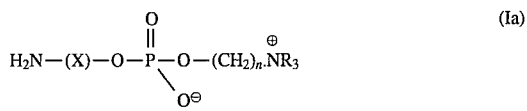

in which the groups R are the same or different and each is a straight or branched $C_1$–$C_4$ alkyl group;

n is from 2 to 6; and

X is selected from the group consisting of straight and branched $C_{1-20}$ alkylene groups, groups of formula —$(CH_2CH_2O)_b$— where b is from 1 to 20, and groups of formula —$(CH_2)_c$—Ar—$(CH_2)_d$— where c and d are the same or different and each is from 0 to 5, Ar is a phenyl ring and the groups $(CH_2)_c$ and $(CH_2)_d$ are positioned on the phenyl ring Ar at the para- or meta-positions, and in which Ar is optionally substituted by one or more $C_1$–$C_4$ alkyl groups, thereby reacting the —$NH_2$ group of the compound of formula (Ia) with the activated surface.

12. A process for treating a polymeric surface of a sight correction device comprising the steps of a) activating the polymeric surface to be treated with a water soluble coupling agent, and b) treating the activated surface with a compound of formula (Ia):

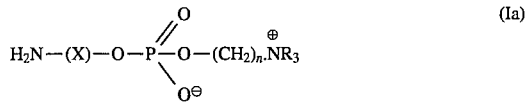

in which the groups R are the same or different and each is a straight or branched $C_1$–$C_4$ alkyl group, n is from 2 to 4, and X is a straight or branched $C_{1-20}$ alkylene group, or X is a group of formula —$(CH_2CH_2O)_b$—, or —$(CH_2)_c$—Ar—$(CH_2)_d$— where b is from 1 to 20, c and d are the same or different and each is from 0 to 5 and Ar is a phenyl ring and the groups $(CH_2)_c$ and $(CH_2)_d$ are positioned on the phenyl ring Ar at the para- or meta- positions, and in which Ar is optionally substituted by one or more $C_1$–$C_4$ alkyl groups, or an acid addition salt thereof or a hydrate thereof.

13. A process according to claim 12, in which n is 2 and each R is methyl.

14. A process according to claim 12, in which X is a group of formula —$(CH_2)_a$—, where a is from 1 to 8, or of formula —$(CH_2CH_2O)_b$—, where b is from 1 to 7, or of formula —$(CH_2)_c$—Ar—$(CH_2)_d$— where c is 0 or 1 and d is 0 or 1.

15. A process according to claim 14 in which the compound of formula (Ia) is 2-((2-aminoethoxyhydroxyphosphinyl)oxy)-N,N,N-trimethylethanaminium hydroxide, inner salt or 2-((6-aminohexyloxyhydroxyphosphinyl)oxy)-N,N,N-trimethylethanaminium hydroxide, inner salt.

16. A process according to claim 12 in which the water soluble coupling agent is a carbodiimide or an isoxazolium-sulphonate.

17. A process according to claim 16 in which the water soluble coupling agent is 1-(3-dimethylaminopropyl)-3-ethyl carbodiimide hydrochloride, and 1-cyclohexyl-3-(2-morpholinoethyl)carbodiimide metho-p-toluene sulphonate or 2-ethyl-5-phenylisoxazolium-3'-sulphonate.

18. A process according to claim 12 in which the polymeric surface of the sight correction device is treated to provide surface carboxyl groups prior to activation with coupling agent.

19. A process according to claim 1 in which the groups R are each a methyl group.

20. A process according to claim 1 in which X represents $-(CH_2)_c-Ar-(CH_2)_d-$ and the $(CH_2)_c$ and $(CH_2)_d$ groups are para position with respect to each other on the phenyl ring Ar.

21. A process according to claim 1 in which Hal in formula (III) is chlorine.

22. A process according to claim 1 in which the groups R are each a methyl group, X represents $-(CH_2)_c-Ar-(CH_2)_d-$ and the $(CH_2)_c$ and $(CH_2)_d$ groups are in para position with respect to each other on the phenyl ring Ar, and Hal in formula (III) is chlorine.

23. A compound according to claim 7 in which X represents $-(CH_2)_c-Ar-(CH_2)_d-$ and the $(CH_2)_c$ and $(CH_2)_d$ groups are in para position with respect to each other on the phenyl ring Ar.

24. A process according to claim 15 in which the groups R are each a methyl group.

25. A process according to claim 10 in which X represents $-(CH_2)_c-Ar-(CH_2)_d-$ and the $(CH_2)_c$ and $(CH_2)_d$ groups are in para position with respect to each other on the phenyl ring Ar.

26. A process according to claim 10 in which the groups R are each a methyl group and X represents $-(CH_2)_c-Ar-(CH_2)_d-$ and the $(CH_2)_c$ and $(CH_2)_d$ groups are in para position with respect to each other on the phenyl ring Ar.

27. A compound according to claim 7, in which each group R is methyl and n is 2.

28. A process according to claim 11 in which the groups R are each a methyl group.

29. A process according to claim 11 in which X represents $-(CH_2)_c-Ar-(CH_2)_d-$ and the $(CH_2)_c$ and $(CH_2)_d$ groups are in para position with respect to each other on the phenyl ring Ar.

30. A process according to claim 11 in which the groups R are each a methyl group and X represents $-(CH_2)_c-Ar-(CH_2)_d-$ and the $(CH_2)_c$ and $(CH_2)_d$ groups are in para position with respect to each other on the phenyl ring Ar.

31. A compound according to claim 7 in which X is a straight chain alkylene of the formula $-(CH_2)_a-$ where a is 1–8.

32. A process according to claim 11, in which X is a straight chain alkylene of the formula $-(CH_2)_a-$ where a is 1–8.

33. A process according to claim 11, in which the water-soluble activating agent is a carbodiimide.

34. A process according to claim 33, in which the carbodiimide is selected from the group consisting of 1-(3-dimethylaminopropyl)-3-ethylcarbodiimide hydrochloride, 1-cyclohexyl-3-(2-morpholinoethyl) carbodiimide metho-p-toluene sulfonate and isoxazolium-sulfonates.

35. A process according to claim 10, in which the surface is a sight correction device.

36. A process according to claim 10, in which Z is B—C(O)— where B is a 5- or 6-membered heteroaromatic ring.

37. A process according to claim 36, in which B is an imidizole.

38. A process according to claim 10, in which Z is 1,3,5-triazine and the surface bears primary or secondary amino groups.

39. A process for the preparation of a compound of formula (Ia):

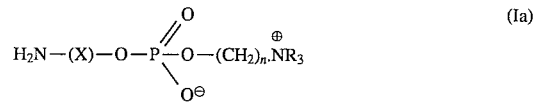

in which the groups R are the same or different and each is a straight or branched $C_1-C_4$ alkyl group;

n is from 2 to 6; and

X is selected from the group consisting of straight and branched $C_{1-20}$ alkylene groups, groups of formula $-(CH_2-CH_2O)_b-$ where b is from 1 to 20, and groups of formula $-(CH_2)_c-Ar-(CH_2)_d-$ where c and d are the same or different and each is from 0 to 5, Ar is a phenyl ring and the groups $(CH_2)_c$ and $(CH_2)_d$ are positioned on the phenyl ring Ar at the para- or meta- positions, and in which Ar is optionally substituted by one or more $C_1-C_4$ alkyl groups, or an acid addition salt thereof or a hydrate thereof, which process comprises reacting a compound of formula (V):

in which X is as hereinbefore defined, or a phosphate salt thereof, with a compound of formula (VI):

in which R is as hereinbefore defined, n is from 2 to 6 and each Hal is the same or different and is halogen, to provide a compound of formula (Ia).

* * * * *